(12) United States Patent
Hahnl et al.

(10) Patent No.: US 11,642,161 B2
(45) Date of Patent: May 9, 2023

(54) CONTINUOUS WOUND DRESSING WITH PLASMA ELECTRODE

(71) Applicant: CINOGY GMBH, Duderstadt (DE)

(72) Inventors: Mirko Hahnl, Berlingerode (DE);
Karl-Otto Storck, Duderstadt (DE);
Leonhard Trutwig, Duderstadt (DE);
Dirk Wandke, Heiligenstadt (DE)

(73) Assignee: CINOGY GMBH, Duderstadt (DE)

( * ) Notice: Subject to any disclaimer, the term of this patent is extended or adjusted under 35 U.S.C. 154(b) by 958 days.

(21) Appl. No.: 16/475,814

(22) PCT Filed: Dec. 20, 2017

(86) PCT No.: PCT/DE2017/101088
§ 371 (c)(1),
(2) Date: Jul. 3, 2019

(87) PCT Pub. No.: WO2018/127255
PCT Pub. Date: Jul. 12, 2018

(65) Prior Publication Data
US 2021/0137578 A1 May 13, 2021

(30) Foreign Application Priority Data
Jan. 6, 2017 (DE) .................... 10 2017 100 192.1

(51) Int. Cl.
*A61B 18/04* (2006.01)
*A61N 1/04* (2006.01)
(Continued)

(52) U.S. Cl.
CPC .......... *A61B 18/042* (2013.01); *A61N 1/0468* (2013.01); *A61N 1/08* (2013.01);
(Continued)

(58) Field of Classification Search
None
See application file for complete search history.

(56) References Cited

U.S. PATENT DOCUMENTS 8,069,817 B2 * 12/2011 Fischer ............. C23C 16/45565
156/345.43
9,889,218 B2 * 2/2018 Morfill ................. H05H 1/2406
(Continued)

FOREIGN PATENT DOCUMENTS

DE 69802094 T2 6/2002
DE 10 2013 226708 A1 6/2015
(Continued)

*Primary Examiner* — Carl H Layno
*Assistant Examiner* — Manolis Pahakis
(74) *Attorney, Agent, or Firm* — WC&F IP (57) ABSTRACT

The invention relates to a treatment device for dielectric harrier discharge plasma treatment of a wound surface or skin surface, having: a flexible, planar electrode assembly with at least one planar electrode (6, 6') and a dielectric layer (5) which at least partially embeds the at least one electrode (6, 6'), has a contact side (7) facing the wound surface or skin surface and electrically shields the planar electrode (6, 6') from the wound surface or skin surface such that only a dielectric barrier current can flow from the electrode (6, 6') to the wound surface or skin surface; and a control device (2) which has a separate housing (25) and via which the electrode (6, 6') can be connected to an operating voltage. The treatment device allows simpler wound treatment in that the assembly of electrode (6, 6') and dielectric layer (5) is designed for uninterrupted contact with the wound surface or skin surface and that the housing (25) of the control device (2) can be fastened with a fastening device (3, 3') to the body having the wound surface or skin surface.

10 Claims, 6 Drawing Sheets

(51) Int. Cl.
*A61N 1/08* (2006.01)
*A61N 1/32* (2006.01)
*A61N 1/44* (2006.01)
*H05H 1/24* (2006.01)
*A61B 18/00* (2006.01)
*A61B 18/14* (2006.01)

(52) U.S. Cl.
CPC ............... *A61N 1/32* (2013.01); *A61N 1/44* (2013.01); *H05H 1/2439* (2021.05); *A61B 2018/00452* (2013.01); *A61B 2018/147* (2013.01); *H05H 1/2418* (2021.05); *H05H 2245/34* (2021.05)

(56) References Cited

U.S. PATENT DOCUMENTS

| | | | | |
|---|---|---|---|---|
| 10,357,580 | B2* | 7/2019 | Trutwig | H01J 37/32568 |
| 10,391,327 | B2* | 8/2019 | Skiera | A61F 2/0077 |
| 10,932,351 | B2* | 2/2021 | Trutwig | A61N 1/04 |
| 2002/0092618 | A1* | 7/2002 | Collins | H01J 37/32165 |
| | | | | 118/723 MW |
| 2003/0168009 | A1* | 9/2003 | Denes | H01J 37/32743 |
| | | | | 156/345.43 |
| 2007/0196591 | A1* | 8/2007 | Yamada | H01L 51/5256 |
| | | | | 427/255.28 |
| 2012/0039747 | A1* | 2/2012 | Morfill | A61L 2/14 |
| | | | | 422/186.05 |
| 2012/0271225 | A1* | 10/2012 | Stieber | A61N 1/44 |
| | | | | 604/23 |
| 2013/0072858 | A1* | 3/2013 | Watson | H01J 37/3244 |
| | | | | 604/23 |
| 2013/0345620 | A1* | 12/2013 | Zemel | A61B 18/042 |
| | | | | 604/24 |
| 2014/0138030 | A1* | 5/2014 | Sawada | H01J 37/32091 |
| | | | | 118/723 E |
| 2014/0182879 | A1* | 7/2014 | Busse | A61N 1/40 |
| | | | | 29/874 |
| 2015/0048739 | A1* | 2/2015 | Forster | H01J 37/32357 |
| | | | | 315/111.21 |
| 2015/0141767 | A1* | 5/2015 | Rogers | A61B 5/6885 |
| | | | | 600/361 |
| 2015/0151135 | A1* | 6/2015 | Kalghatgi | A61M 37/00 |
| | | | | 604/20 |
| 2015/0157870 | A1* | 6/2015 | Kalghatgi | A61F 7/02 |
| | | | | 604/23 |
| 2015/0202452 | A1* | 7/2015 | Skiera | A61F 2/78 |
| | | | | 604/23 |
| 2015/0343231 | A1* | 12/2015 | Sanders | A61N 1/44 |
| | | | | 607/2 |
| 2016/0236002 | A1* | 8/2016 | Dirk | A61N 1/44 |
| 2016/0271411 | A1* | 9/2016 | Hummel | A61N 1/44 |
| 2016/0287892 | A1* | 10/2016 | Nettesheim | A61N 1/0468 |
| 2016/0331989 | A1* | 11/2016 | Cho | A61N 1/326 |
| 2017/0021172 | A1* | 1/2017 | Perez | A61B 5/42 |
| 2017/0080207 | A1* | 3/2017 | Perez | A61F 5/0003 |
| 2017/0107505 | A1* | 4/2017 | Birmingham | C12M 47/06 |
| 2017/0128117 | A1* | 5/2017 | Myers | H05H 1/2406 |
| 2017/0136252 | A1* | 5/2017 | Weltmann | A61L 2/14 |
| 2017/0213701 | A1* | 7/2017 | Subramani | H01J 37/32577 |
| 2017/0231680 | A1* | 8/2017 | Mahrenholz | A61B 18/085 |
| | | | | 606/34 |
| 2018/0056057 | A1* | 3/2018 | Kalita | A61N 1/0492 |
| 2018/0125689 | A1* | 5/2018 | Perez | A61N 1/36014 |
| 2018/0140824 | A1* | 5/2018 | Pemen | A61N 1/0468 |
| 2018/0178024 | A1* | 6/2018 | Hahnl | A61N 1/32 |
| 2018/0214586 | A1* | 8/2018 | Louis | A61L 2/186 |
| 2018/0221517 | A1* | 8/2018 | Trutwig | A61B 18/042 |
| 2018/0295708 | A1* | 10/2018 | Trutwig | A61N 1/04 |
| 2019/0070407 | A1* | 3/2019 | Kim | A61B 18/042 |
| 2019/0110933 | A1* | 4/2019 | Weltmann | A61N 1/44 |
| 2019/0115189 | A1* | 4/2019 | Patton | H01J 37/32577 |
| 2019/0223280 | A1* | 7/2019 | Wandke | A61N 1/44 |
| 2019/0308027 | A1* | 10/2019 | Hahnl | A61N 1/0492 |
| 2019/0327823 | A1* | 10/2019 | Hahnl | A61N 1/326 |
| 2020/0029414 | A1* | 1/2020 | Trutwig | H05H 1/2406 |
| 2020/0170098 | A1* | 5/2020 | Wandke | H05H 1/2406 |
| 2020/0187341 | A1* | 6/2020 | Wandke | A61L 2/0011 |
| 2020/0297881 | A1* | 9/2020 | Weltmann | A61L 2/0011 |
| 2021/0112651 | A1* | 4/2021 | Lee | A61N 1/0476 |
| 2021/0136904 | A1* | 5/2021 | Trutwig | A61N 1/0468 |
| 2021/0299436 | A1* | 9/2021 | Kalita | A61N 1/0496 |
| 2021/0385933 | A1* | 12/2021 | Eckert | A61B 18/042 |

FOREIGN PATENT DOCUMENTS

| | | | | |
|---|---|---|---|---|
| DE | 10 2014 013716 A1 | 3/2016 | | |
| DE | 10 2014 220488 A1 | 4/2016 | | |
| EP | 2 170 022 A1 | 3/2010 | | |
| WO | 2015/091070 A1 | 6/2015 | | |
| WO | WO-2016037599 A1 * | 3/2016 | ........... | A61B 18/042 |
| WO | WO-2017067535 A1 * | 4/2017 | ........... | A61L 2/0011 |

* cited by examiner

CONTINUOUS WOUND DRESSING WITH PLASMA ELECTRODE

CROSS-REFERENCE TO RELATED APPLICATIONS

This application is a Rule 371 filing from PCT/DE2017/101088 filed Dec. 20, 2017, which claimed priority to German Application 10 2017 100 192.1 filed Jan. 6, 2017.

FIELD OF THE INVENTION

The invention relates to a treatment apparatus for a dielectric barrier plasma treatment of a wound surface or skin surface, having a flexible planar electrode arrangement with at least one planar electrode and a dielectric layer, which at least partially embeds the at least one electrode, which comprises an application side facing toward the wound surface or skin surface, and electrically shields the planar electrode from the wound surface or skin surface in such a way that only a dielectric barrier current can flow from the electrode to the wound surface or skin surface, and having a control apparatus, which comprises a separate housing and by means of which the electrode can be connected to an operating voltage.

BACKGROUND OF THE INVENTION

Such a treatment apparatus is known from DE 10 2014 013 716 A1. The flexible planar electrode arrangement is in this case configured in such a way that it can be applied with its application side directly on a wound surface. To this end, the dielectric itself is formed from a wound-compatible material, or the dielectric is provided on the application side with a wound-healing layer, which may be as a conventional cellulose lint layer or alternatively as a layer of an open-pored solid matrix of a hygienic or wound-healing material. The layer may in this case be grown directly on the dielectric. Because of the open-pored nature of the layer, the desired plasma may be formed in the material of the matrix. The dielectric itself may be provided on the application side with a structure which can, for example, consist of pimples and be applied on the wound surface, and forms between it air cavities in which the plasma can be set up on the basis of the electrical driving of the electrode. In the known treatment apparatus, the planar electrode arrangement may be configured as an integral application piece and have a tongue-shaped appendage with which the application piece can be insertable into a reception slot of the housing, configured as a handle, of the control apparatus. In the inserted state, the electrode may be contacted with the operating voltage formed in the control apparatus in the form of high-voltage signals suitable for plasma formation. Both the dielectric layer and the planar electrode may in this case be provided with through-openings which are suitable both for aspiration of fluid from the wound region and for injecting gases that promote wound healing.

The known treatment apparatus is suitable for disinfecting the wound surface with a short-term plasma treatment, so that after this a conventional wound covering, optionally impregnated with a medicament that promotes wound healing, can in turn be applied for a few hours. After this, the wound dressing is removed again and a further plasma treatment is carried out with the treatment apparatus, in order to avoid proliferation of microorganisms in the wound surface, or in the wound secretion. Besides the disinfecting effect, microcirculation in the skin is stimulated by the plasma treatment.

It is therefore also known to apply a plasma treatment to a skin surface which is not affected by a wound in order, besides the disinfecting effect, in particular to achieve a healing or toning effect by increased microcirculation.

SUMMARY OF THE INVENTION

The object of the present invention is to refine a treatment apparatus of the type mentioned in such a way that an improved treatment of a wound surface or skin surface is possible.

In order to achieve this object, according to the invention a treatment apparatus of the type mentioned in the introduction is characterized in that the arrangement consisting of electrode and dielectric layer is configured for uninterrupted application on the wound surface or skin surface, and in that the housing of the control apparatus can be fastened by a fastening device on the body comprising the wound surface or skin surface.

The treatment apparatus according to the invention is therefore configured to be applied with the electrode arrangement consisting of electrode and dielectric layer continuously onto the wound surface or skin surface, i.e. not just for the time of the treatment of the wound surface or skin surface with a plasma for the purpose of killing germs and/or stimulating microcirculation in the tissue. The previously conventional change between a conventional wound dressing and the application of an electrode arrangement in order to carry out a disinfecting plasma treatment of the wound surface is therefore obviated. In order that the arrangement consisting of electrode and dielectric layer is suitable as an in this sense continuous dressing on a wound surface or skin surface, the arrangement is configured in such a way that an accumulation of wound secretion on the application side can be discharged via the through-openings. This is assisted by the fact that absorbent material is arranged on the upper side of the dielectric layer, which lies opposite the application side, with which wound secretion is transported from the application side of the arrangement via through-openings in order to remain on the upper side of the dielectric layer. Provision is preferably made for the transport of wound secretion away from the wound surface to be promoted in a manner known per se by reduced pressure formation by means of a suction pump. For the treatment of a skin surface not provided with a wound surface, the through-openings may optionally be used to deliver a therapeutic substance.

In order that the treatment apparatus according to the invention is suitable for a continuous wound or skin dressing, the control apparatus is preferably fastened on the body, comprising the wound surface or skin surface, of the living being in the immediate vicinity of the arrangement, used as a wound or skin dressing, consisting of electrode and dielectric layer. In this way, it is possible for the wearer of the treatment apparatus to remain mobile during the wound healing or skin treatment, and to have freedom of movement as with a conventional wound dressing which does not offer the possibility of plasma treatment. In this case, the control apparatus is configured to be small and lightweight, and may preferably be fastened directly on the body, for example by an attachment loop, which is for example placed around the neck, and/or with the aid of a suction cup with which fastening on the skin is possible in the manner of ECG electrodes. It is of course also possible to adhesively bond the control apparatus onto the skin with conventional bandage adhesives. In this case, the adhesive bond may be provided on its own or in combination with mechanical fastening. The type of fastening which is appropriate in an individual case is dictated by the position of the wound surface or skin surface and the fastening opportunities existing in the environment of the wound surface or skin surface. In each case, a short distance between the dressing arrangement consisting of electrode and dielectric layer, on the one hand, and the control apparatus on the other hand, is sought, in particular when a high-voltage signal (peak voltage of a few kV) is transmitted through this connection.

In order to permit effective aspiration, in one embodiment of the treatment apparatus provision is made for the dielectric layer to be provided with through-openings, and the arrangement consisting of electrode and dielectric layer is covered in a gas-tightly sealed manner with an airtight cover in the region of the through-openings and thus delimits a fluid space communicating with the through-openings, that a line is connected to the cover. In this case, the control apparatus may contain a pump which can be connected to the fluid space by means of the line. In this embodiment, the treatment apparatus itself comprises the pump, with which for example aspiration of wound secretion may be carried out, without the handleability of the treatment apparatus and the patient's mobility thereby being impaired.

The aspirated liquid may be collected in the aspiration space above the dielectric layer, when the aspiration space is at least partially filled with a liquid-absorbent material.

In another embodiment, the pump is preceded in the flow path in the control apparatus by a container for receiving fluid transported by the pump. In this way, it is also possible to treat wound surfaces which exude large quantities of wound secretion. The container is preferably connected replaceably to the pump and/or the housing. In this case, it is advantageous for there to be a gas-permeable, liquid-retaining filter in the container in the flow path toward the pump. This ensures that no aspirated liquid enters the pump, but instead is retained in the container. If the container is fastened replaceably, the control apparatus can readily be employed for a further use. Since the components of the control apparatus are inexpensive mass-produced components, for certain applications it may be expedient to dispense with sterilization of the control apparatus after use and to dispose of the control apparatus together with the application piece formed by electrode and dielectric layer.

The described arrangement with the through-openings and an airtight cover is suitable not only for carrying out aspiration, but also for delivering a therapeutic or skin-hygiene substance into the region of the skin surface in which the plasma treatment is carried out. In this way, the plasma treatment may possibly be effectively enhanced because the ability of the skin to take up delivered therapeutic or hygienic substances is increased significantly by the plasma treatment. The delivery of the substance may in this case be carried out in an automated manner if the control apparatus comprises a delivery pump therefor, the switching on and off of said pump being controlled by a microcontroller, preferably in coordination with periods of the plasma treatment.

For the treatment apparatus, it may be advantageous that the arrangement consisting of electrode and dielectric layer forms a tongue-shaped connecting piece, which can be inserted as a narrow web and fixed in a reception slot of the control apparatus in order to establish an electrical connection between the operating voltage and the electrode. In this way, direct contacting of the electrode is possible without a connecting cable being required therefor. The connection between the arrangement and the control apparatus may be configured to be releasable by means of a control button.

In one embodiment of the treatment apparatus, the at least one electrode and the dielectric layer are contained in an integral application piece. The application piece is configured according to the invention as a continuous wound or skin dressing.

In one embodiment of the control apparatus, the operating voltage delivered in the control apparatus to the electrode is formed by high-voltage signals, with which the dielectric barrier plasma discharge is created on the application side of the dielectric layer, the body functioning as a counter electrode in the region of the wound surface or skin surface In another embodiment, the operating voltage delivered in the control apparatus to the electrode is an AC voltage, which does not yet represent a high voltage but reaches the electrode by a high-voltage stage, the high-voltage stage being arranged on the application piece or being integrated into the application piece. One advantage of this arrangement is that the high voltage can be generated directly at the electrode and therefore does not need to be conducted from the control apparatus to the electrode via a connecting piece.

The advantages of the treatment apparatus according to the invention are further enhanced when the control apparatus comprises a battery voltage supply, the output DC voltage of which is converted into AC voltage signals in the control apparatus by an inverter stage. The battery voltage supply may in this case be formed by conventional disposable batteries, but also by rechargeable batteries (accumulators).

BRIEF DESCRIPTION OF THE DRAWINGS

The invention will be described in more detail below with the aid of exemplary embodiments represented in the drawing, in which.

DETAILED DESCRIPTION OF THE INVENTION

Figure 1:
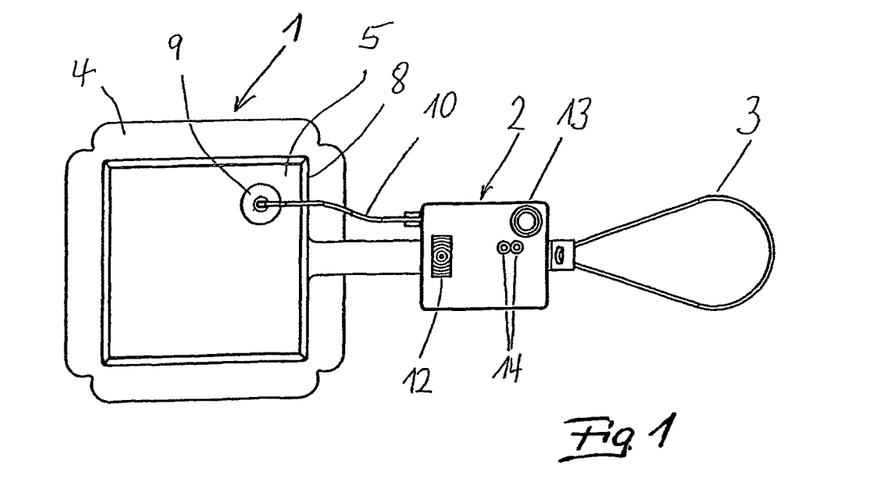
FIG. 1 shows a schematic plan view of a first embodiment of a treatment apparatus having an aspiration device.
Figure 2:
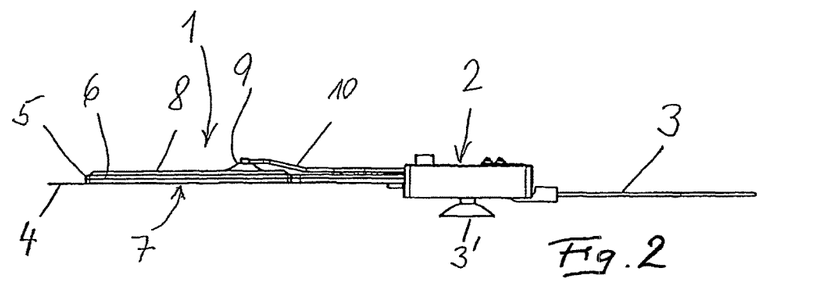
FIG. 2 shows a side view of the treatment apparatus according to FIG. 1.
Figure 3:
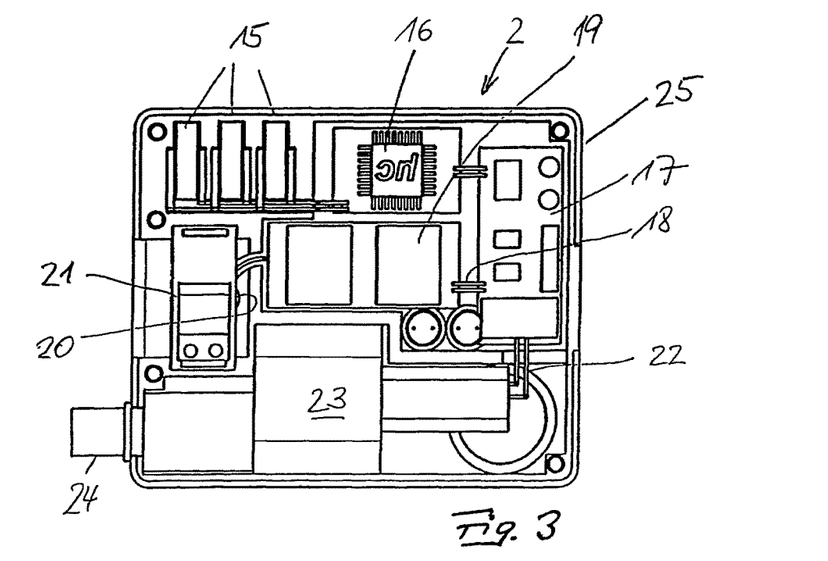
FIG. 3 shows a schematic representation of the construction of the control apparatus of the first embodiment.

The first embodiment, represented in FIGS. 1 to 3, shows an application piece 1 which is connected directly to a control apparatus 2. The control apparatus 2 is provided with a fastening device 3 in the form of a fastening loop, in order to apply the control apparatus 2 on a patient's body.

The application piece 1 consists of a frame-shaped edge piece 4, which is provided on a lower side with a pressure-sensitive adhesive and is provided for adhesive application on a patient's skin, optionally around a wound surface. The edge piece 4 protrudes on all sides beyond a dielectric layer 5, which is configured in a planar and flexible manner and embeds a planar and flexible electrode 6 and shields against contact on all sides. The dielectric layer 5 prevents a direct galvanic current flowing from the electrode 6 to the patient's skin, which acts as a counter electrode, when the dielectric layer is applied with its lower side (application side 7) on the patient's skin in the region of a wound surface or skin surface. On the upper side of the dielectric layer 5, i.e. on the side opposite the application side, the dielectric layer 5 is covered in an airtight manner with a gas-tight cover 8. The cover does not reduce the flexibility of the application piece 1 and is, for example, configured in the form of a film. A suction cup 9, to which a tube line 10 that leads to the control apparatus 2 is connected, is arranged on an opening of the cover 8.

The electrode 6 and the dielectric layer 5 together form a tongue-shaped appendage 11, with which the electrode 6 enclosed by the dielectric layer 5 is inserted into the control apparatus 2. The control apparatus 2 is provided with a button 12, by which the connection of the tongue-shaped appendage 11 to the control apparatus 2 can be released. FIG. 1 furthermore shows an on/off button 13 and also two display lights 14 for displaying operating states of the control apparatus 2.

FIG. 2 furthermore illustrates that the control apparatus 2 may also be fixed on the patient's body by means of a further fastening device 3', here in the form of a suction cup. The fastening devices 3 and 3' therefore cooperate in order to fix the control apparatus 2 on the patient's body. The control apparatus 2 represented in FIG. 3 is represented as a wireless apparatus and comprises three batteries 15, with which a battery supply voltage is produced. The supply voltage from the batteries 15 travels to a microcontroller 16, which controls the running of the control apparatus 2. The microcontroller 16 controls an inverter stage 17 with which, in a manner known per se, an AC voltage with an increased peak voltage of for example 250V is generated from the DC voltage of the batteries 15. The inverter stage 17 supplies, via a first output 18, a high-voltage stage 19 in which high-voltage pulses of a few tens of kV with opposite polarity are generated. This is carried out in a manner known per se with the aid of discharge paths (not shown) which, when a threshold voltage is exceeded, ignite and cause a current pulse through a primary coil. A secondary coil wound with a suitable transformer ratio makes it possible to form a high-voltage pulse at its output, which is conducted to a contact 20 of a contact instrument 21. The contact instrument 21 may be locked and unlocked by the button 12.

A second output 22 of the inverter stage 17 supplies a suction pump 23, which protrudes with a tube adapter 24 out from a housing 25 enclosing the control apparatus 2 and allows connection to the tube line 10.

The switching of the high-voltage supply on and off by the high-voltage stage 19 may expediently be controlled by a program stored in the microcontroller 16. For example, the plasma treatment may be carried out over a duration of from 1 to 2 minutes, which may respectively be followed by a pause of several hours. Furthermore, the aspiration by the suction pump 23 may suitably be controlled periodically, for example in each case for a few seconds at time intervals of between 10 and 60 minutes in the case of acutely weeping wounds.

Figure 4:
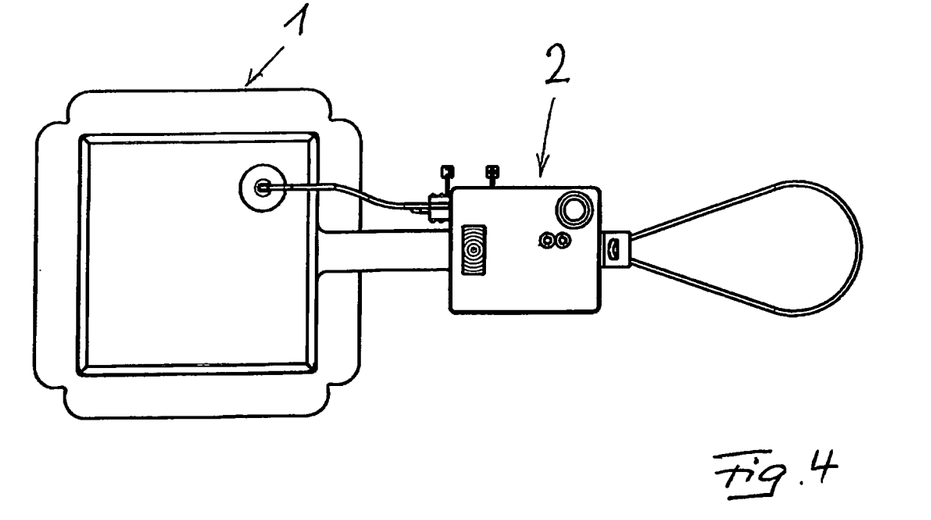
FIG. 4 shows a schematic plan view of a second embodiment of a treatment apparatus.
Figure 5:
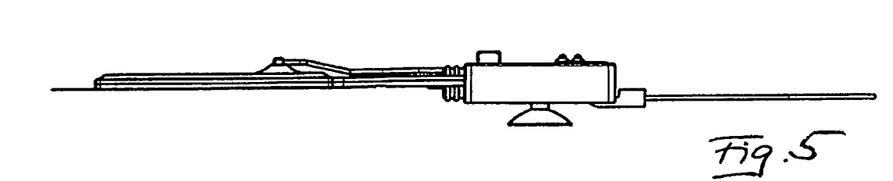
FIG. 5 shows a side view of the embodiment according to FIG. 4.
Figure 6:
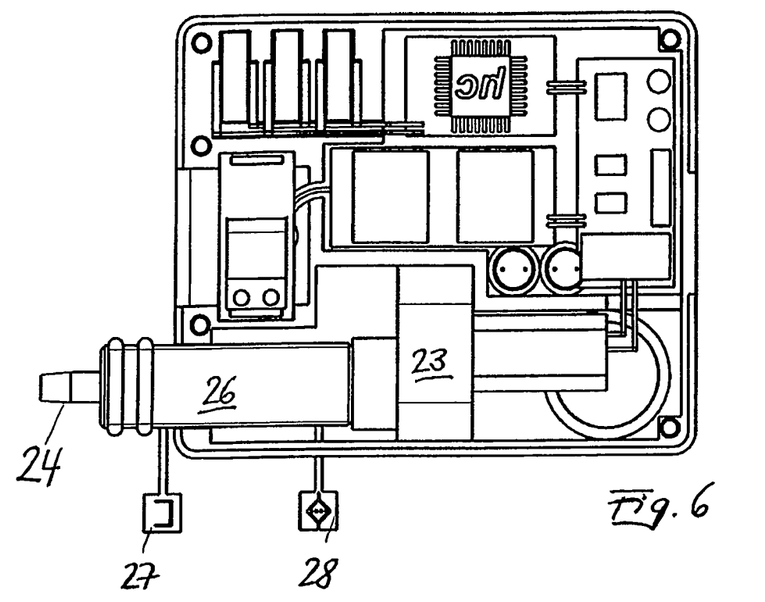
FIG. 6 shows a schematic representation of the construction of the control apparatus according to the second embodiment.

In the embodiment represented in FIGS. 4 to 6, an almost identical construction of the application piece 1 and of the control apparatus 2 is produced. The only difference is that the suction pump 23 comprises an attached container 26, which comprises a reception chamber (illustrated by symbol 27) and a filter (illustrated by symbol 28). Aspirated liquid is collected in the reception chamber 27 of the container 26. The filter 28 prevents the aspirated liquid from entering the suction pump 23. After the end of the treatment, the container 26 may be released from the pump 23 and disposed of with the aspirated liquid. FIG. 6 shows that the container 26 is arranged between the pump 23 and the connection adapter 24.

Figure 7:
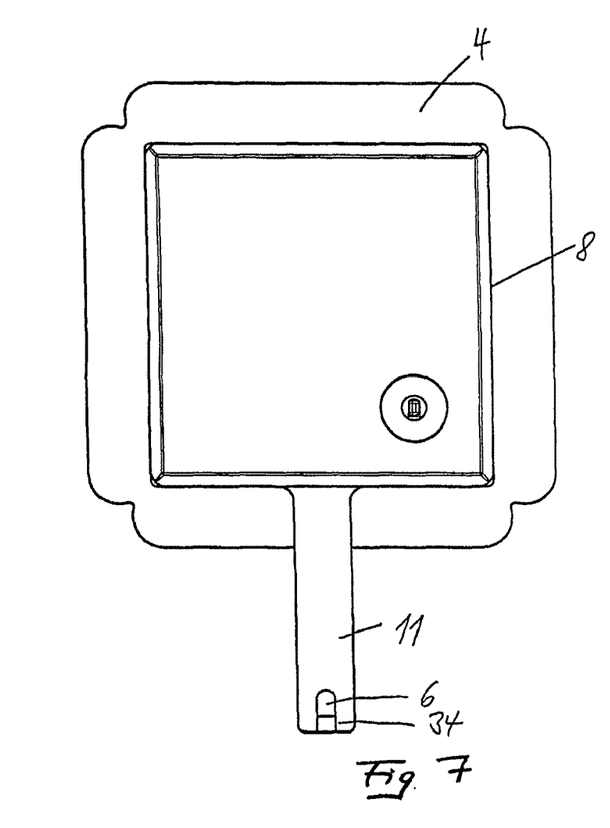
FIG. 7 shows a plan view of an application piece for the first and second embodiments.
Figures 8, 9:
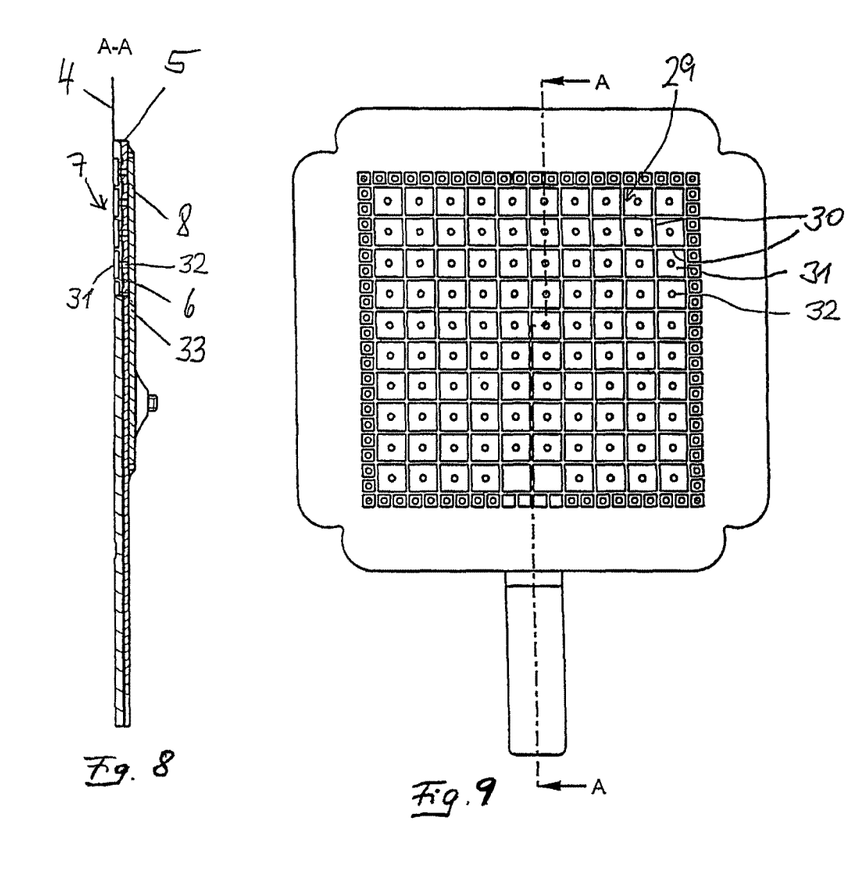
FIG. 8 shows a height section through the application piece.
FIG. 9 shows a view of the application piece from the application side (from below)

FIGS. 7 to 9 illustrate the construction of the application piece 1 in an enlarged representation. In particular, it can be seen that the dielectric layer 5 forms a grid-like structure 29 on the application side 7, which structure is formed by mutually perpendicular intersecting webs 30 of equal height. Chambers 31 open toward the application side 7 are thereby formed, which are shielded on their upper side by a continuous sheet of the dielectric layer 5 from the electrode 6 embedded in the dielectric layer 5. The shape of the chambers 31 may also be configured as a rhombus, a honeycomb or also round. Centrally in the chambers 31, the dielectric layer respectively comprises a through-opening 32, which open into an aspiration space 33 that is delimited by the cover 8 on the one hand and the dielectric layer 5 on the other hand. The aspiration space 33 may be filled with an absorbent material which transmits the air aspiration flow through the suction pump 23 but stops the aspirated liquid. Filling of the aspiration space 33 with a liquid-absorbing material is advantageous in particular when, according to the first embodiment, the suction pump 23 is used without a preceding container 26.

The sectional representation of FIG. 8 shows that the electrode 6 also comprises through-openings, which are aligned with the through-openings 32 but have a larger diameter so that the dielectric layer 5 continuously forms the wall of the through-openings 32, so that direct contact of liquid with the electrode 6 carrying the high voltage cannot take place. The thickness, located in the through-openings 32, of the dielectric layer 5 is large enough that voltage breakdowns or microdischarges are reliably avoided.

FIGS. 7 and 9 show that the cover 8 extends over the entire region of the electrode 6 and of the dielectric layer 5 in which the through-openings 32 are located. The aspiration space 33 therefore communicates with the through-openings 32, but in other regards seals the dielectric layer 5 in the region of the aspiration space 33 in a gas-tight manner.

The tongue-shaped appendage 11 which can be seen in FIG. 7 contains a strip-shaped appendage of the electrode 6, which appendage is fully enclosed by the dielectric layer 5 with the exception of the recess 34 which can be seen in FIG. 7, through which a small piece of the electrode 6 is exposed toward the upper side. The tongue-shaped appendage 11 is inserted into the corresponding reception slot of the control apparatus 2, so that the contacting with the contact 20 can take place at a distance from the slot inside the housing 25 of the control apparatus.

Figure 10:
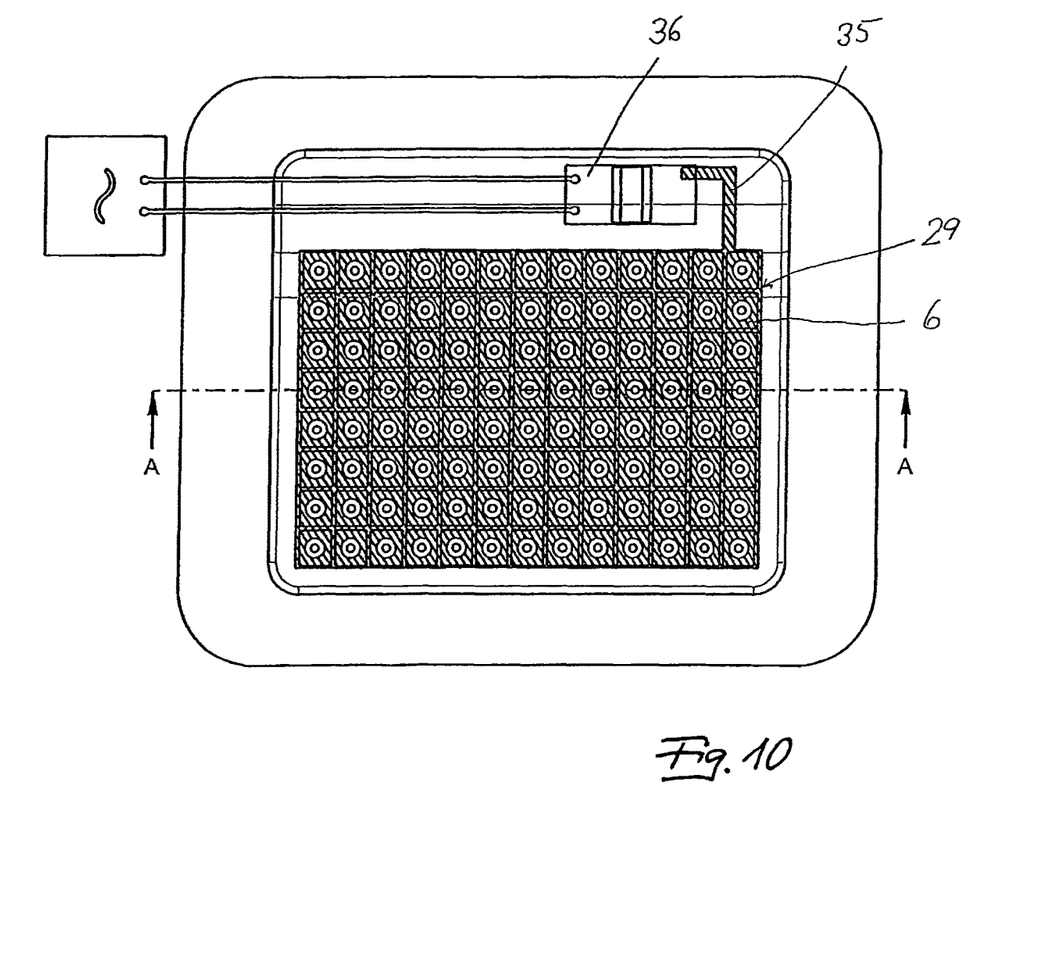
FIG. 10 shows a view from below of an application side of an electrode arrangement having a single planar electrode, a high-voltage stage being integrated into the dielectric layer.
Figure 11:
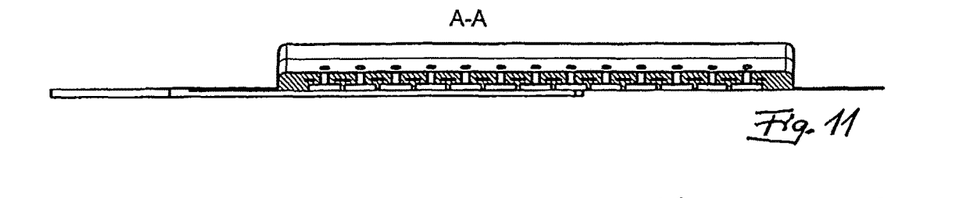
FIG. 11 shows a height section through the arrangement according to FIG. 10.

FIGS. 10 and 11 show the application piece 1 from the application side, where the dielectric layer comprises the grid structure 29. Also extending in the region of the grid structure 29 is the extent of the electrode 6, which in this exemplary embodiment is connected by a flat appendage 35 to the output of a high-voltage stage 36, which in this embodiment is located inside the dielectric layer 5 in the application piece 1. Accordingly, the application piece 1 according to FIG. 10 is merely supplied with an AC voltage, such as is available for example at the outputs 18, 22 of the inverter stage 17 in the embodiments of FIGS. 1 to 6.

The high-voltage stage 36 is preferably integrated into the material of the dielectric layer 5, which to this end may be configured with an enlarged thickness at the edge in which the high-voltage stage 36 is located, as illustrated in the sectional representation of FIG. 11, in which the relevant edge can be seen as a view.

It is readily apparent that the inverter stage 17 too may be integrated into the material of the dielectric layer 5, so that the control apparatus 2 in this case would merely have to deliver the DC voltage supply.

It is furthermore clear to the person skilled in the art that not only integration of the high-voltage stage 36 and optionally the inverter stage 17 into the material of the dielectric layer 5 is possible, but also arrangement of the high-voltage stage 36 and optionally the inverter stage 17 with microcomponents on the dielectric layer 5 as a carrier, if a cover, preferably in flexible form, is applied onto the dielectric layer 5 in this case in order to ensure contact protection of the components.

Figure 12:
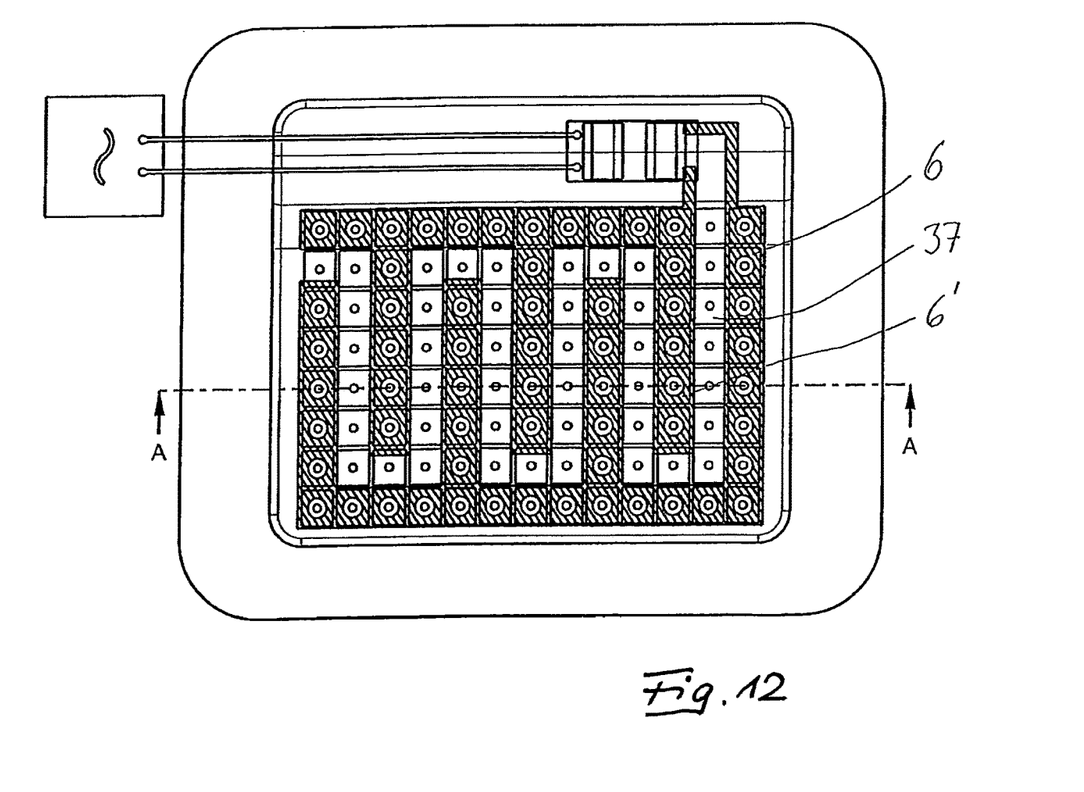
FIG. 12 shows a view of the application side of an electrode arrangement having two electrodes, both of which are supplied in phase opposition with high-voltage signals which are generated in a high-voltage stage which is integrated into the application piece.
Figure 13:
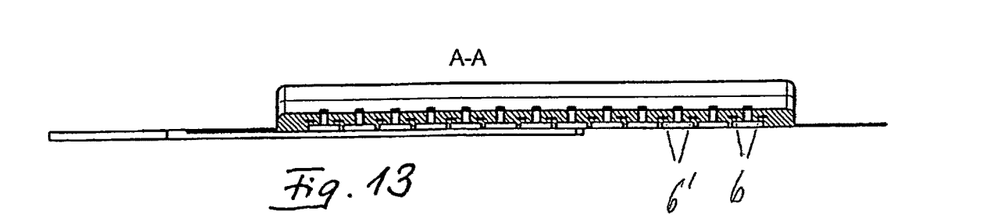
FIG. 13 shows a height section along the line A-A in FIG. 12.

In the modification of the application piece as represented in FIGS. 12 and 13, two electrodes 6, 6' are provided which are separated from one another by insulating sections 37 of the dielectric layer 5.

The two electrodes 6, 6' preferably both operate as high-voltage electrodes and are driven with oppositely poled high-voltage pulses. The effect of the plasma field is due to the fact that both electrodes use the patient's body as a counter electrode, but between the two electrodes there is an enhanced electric field which amplifies and promotes the plasma formation.

It is, however, also conceivable to connect the electrodes 6, 6' in such a way that the electrode 6' functions as a counter electrode for the electrode 6, so that the plasma field is formed only by a surface discharge between the electrodes 6, 6'. For a wound treatment, however, in almost all cases it is appropriate to use the skin with the patient's wound as a counter electrode.

Figure 14:
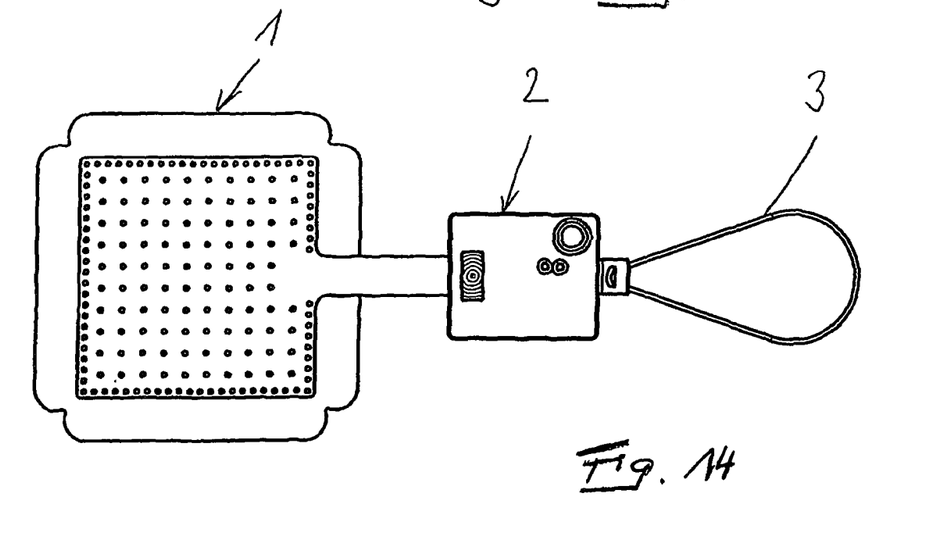
FIG. 14 shows a plan view of a third embodiment of the treatment apparatus, in which no aspiration with a pump takes place.
Figure 15:
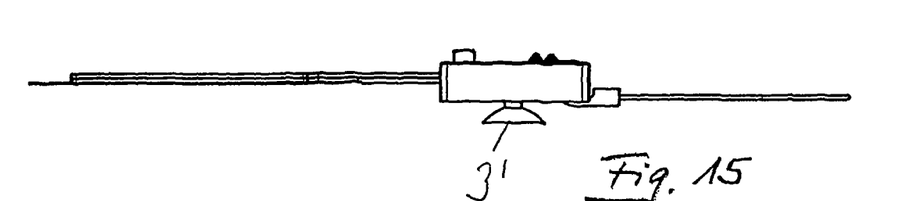
FIG. 15 shows a side view of the embodiment according to FIG. 14.
Figure 16:
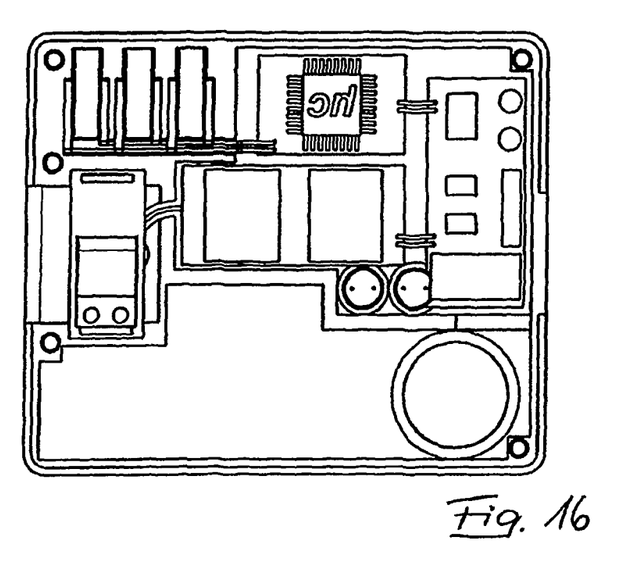
FIG. 16 shows a schematic representation of the construction of the control apparatus for the third embodiment.

The embodiment represented in FIGS. 14 to 16 corresponds to the embodiment according to FIG. 1, but without suction pump 23. The removal of the wound secretion via the through-openings 32 is in this case carried out exclusively by the absorbent material in the aspiration space 33.

The described embodiments do not restrict the possible refinements of the treatment apparatus according to the invention. In particular, it is not necessary to contact the application piece 1 directly with the control apparatus via the tongue-shaped appendage 11. Furthermore, it is not necessary to produce a releasable connection between application piece 1 and control apparatus 2, if the control apparatus 2 is disposed of together with the application piece 1 after the end of the treatment. In this case, a fixed or clamping, non-releasable connection between application piece 1 and control apparatus 2 is possible and appropriate.

The invention claimed is:

1. A treatment apparatus for a dielectric barrier plasma treatment of a wound surface or skin surface, comprising:
    a flexible planar electrode arrangement with at least one planar electrode and a dielectric layer, wherein the at least one planar electrode is at least partially embedded in the dielectric layer, wherein the flexible planar electrode arrangement comprises an application side configured to face toward the wound surface or skin surface, and electrically shield the at least one planar electrode from the wound surface or skin surface in such a way that only a dielectric barrier current can flow from the at least one planar electrode to the wound surface or skin surface, wherein the dielectric layer includes a plurality of through-openings;
    an air tight cover positioned over the through-openings in the dielectric in a gas-tight sealed manner which delimits a fluid space communicating with the through-openings;
    a line connected to the cover;
    a control apparatus which contains a pump and comprises a separate housing, by means of which the at least one planar electrode is connectable to an operating voltage; and
    a container for receiving or releasing liquid transported by the pump which is replaceably connected to one or more of the pump and the housing,
    wherein the pump is connectable to the fluid space by the line connected to the cover,
    wherein the flexible planar electrode arrangement is configured for uninterrupted application on the wound surface or skin surface, and
    wherein the housing of the control apparatus is fastenable by a fastening device on a body comprising the wound surface or skin surface.

2. The treatment apparatus as claimed in claim 1, wherein the fluid space is at least partially filled with a liquid-absorbent material.

3. The treatment apparatus as claimed in claim 1, wherein a flow path in the control apparatus has the container preceding the pump.

4. The treatment apparatus as claimed in claim 3, further comprising a gas-permeable, liquid-retaining filter in the container in the flow path toward the pump.

5. The treatment apparatus as claimed in claim 1, wherein the flexible planar electrode arrangement forms a tongue-shaped connecting piece which is insertable as a narrow web and fixable in a reception slot of the control apparatus in order to establish an electrical connection between the operating voltage and the at least one planar electrode.

6. The treatment apparatus as claimed in claim 1, further comprising a control button for releasing a connection between the flexible planar electrode arrangement and the control apparatus.

7. The treatment apparatus as claimed in claim 1, wherein the control apparatus is configured to permit the operating voltage delivered to the at least one planar electrode to include high-voltage signals.

8. The treatment apparatus as claimed in claim 1, wherein the at least one planar electrode and the dielectric layer are contained in an integral application piece.

9. The treatment apparatus as claimed in claim 1, wherein the control apparatus is configured to permit the operating voltage delivered to the at least one planar electrode to be an alternating current (AC) voltage which reaches the at least one planar electrode via a high-voltage stage which is arranged on the application piece.

10. The treatment apparatus as claimed in claim 1, wherein the control apparatus comprises a battery voltage supply which provides an output direct current (DC) voltage which is converted into alternating current (AC) voltage signals in the control apparatus by an inverter stage.

\* \* \* \* \*